US012760236B2

(12) United States Patent
Keller et al.

(10) Patent No.: US 12,760,236 B2
(45) Date of Patent: Oct. 13, 2026

(54) SYSTEMS AND METHODS OF PRODUCING SYNTHESIS GAS AND BIO-OIL FROM BIOMASS

(71) Applicants: Arnold Keller, Henderson, NV (US); Michael Keller, Henderson, NV (US)

(72) Inventors: Arnold Keller, Henderson, NV (US); Michael Keller, Henderson, NV (US)

( * ) Notice: Subject to any disclaimer, the term of this patent is extended or adjusted under 35 U.S.C. 154(b) by 693 days.

(21) Appl. No.: 18/156,930

(22) Filed: Jan. 19, 2023

(65) Prior Publication Data

US 2024/0010919 A1 Jan. 11, 2024

Related U.S. Application Data

(63) Continuation-in-part of application No. 17/941,653, filed on Sep. 9, 2022, now abandoned.

(Continued)

(51) Int. Cl.

*C10L 9/08* (2006.01)
*B01J 19/24* (2006.01)

(Continued)

(52) U.S. Cl.

CPC ............. *C10L 9/086* (2013.01); *B01J 19/245* (2013.01); *C01B 3/12* (2013.01); *C01B 3/50* (2013.01); *C12M 43/02* (2013.01); *C01B 2203/0283* (2013.01); *C01B 2203/0475* (2013.01); *C01B 2203/0883* (2013.01); *C01B 2203/86* (2013.01);

(Continued)

(58) Field of Classification Search

CPC ................................................ C10J 2300/0916

See application file for complete search history.

(56) References Cited

U.S. PATENT DOCUMENTS 4,166,802 A * 9/1979 Slater ........................ C10J 3/485 252/373
5,188,740 A * 2/1993 Khan ..................... C10K 1/005 210/768

(Continued)

FOREIGN PATENT DOCUMENTS

CN 110394122 A 11/2019
WO 2014022218 A1 2/2014
WO 2022094682 A1 5/2022

OTHER PUBLICATIONS

PCT Search Report and Written Opinion dated Jan. 4, 2024 for related PCT Patent Application No. PCT/US2023/068315, 21 pages.

(Continued)

*Primary Examiner* — Imran Akram
(74) *Attorney, Agent, or Firm* — Hovey Williams LLP; Kameron D. Kelly

(57) ABSTRACT

A system and method of producing synthesis gas and bio-oil from biomass. The method comprises producing, in a gasification unit, synthesis gas from a carbonaceous feedstock, optionally cooling the synthesis gas discharged from the gasification unit, channeling the synthesis gas towards a hydrothermal processing unit, wherein the hydrothermal processing unit is configured to process a biomass feedstock contained in a pressurized water stream, transferring, in the hydrothermal processing unit, heat from the synthesis gas to the biomass feedstock, and producing a hydrothermal product from the biomass feedstock in the pressurized water stream.

25 Claims, 6 Drawing Sheets

Related U.S. Application Data

(60) Provisional application No. 63/359,317, filed on Jul. 8, 2022.

(51) Int. Cl.
*C01B 3/12* (2006.01)
*C01B 3/50* (2026.01)
*C12M 1/00* (2006.01)

(52) U.S. Cl.
CPC .................. *C10J 2300/0906* (2013.01); *C10J 2300/0916* (2013.01); *C10J 2300/1612* (2013.01); *C10J 2300/1643* (2013.01); *C10J 2300/1675* (2013.01); *C10J 2300/1681* (2013.01); *C10J 2300/1884* (2013.01); *C10L 2290/04* (2013.01); *C10L 2290/06* (2013.01); *C10L 2290/10* (2013.01)

(56) References Cited

U.S. PATENT DOCUMENTS

| | | | |
|---|---|---|---|
| 9,758,728 | B2 | 9/2017 | Elliott et al. |
| 10,920,150 | B2 | 2/2021 | Chiaberge et al. |
| 2011/0111475 | A1 | 5/2011 | Kuhry et al. |
| 2011/0232160 | A1 | 9/2011 | Siskin et al. |
| 2014/0102002 | A1 | 4/2014 | Furusjo et al. |
| 2016/0208396 | A1* | 7/2016 | Takeda ...................... C25B 9/17 |
| 2019/0048359 | A1* | 2/2019 | Laqua ................ C12N 15/8203 |
| 2019/0330562 | A1 | 10/2019 | Burattini |
| 2020/0291314 | A1* | 9/2020 | Furusjö .................... C10G 2/32 |
| 2021/0198615 | A1 | 7/2021 | Harmon et al. |
| 2022/0072519 | A1 | 3/2022 | Chen et al. |
| 2022/0315470 | A1* | 10/2022 | Haddad .................. C02F 11/18 |

OTHER PUBLICATIONS

Diego Lopez Barreiro et al., Hydrothermal liquefaction (HTL) of microalgae for biofuel production: State of the art review and future prospects, Biomass and Bioenergy 53 (2013), pp. 113-127, Ghent, Belgium.

Madeleine Stone, Can food crops grow in the dark? Scientists are working out how, National Geographic Partners, LLC, https://www.nationalgeographic.com, Aug. 2, 2022, 16 pages.

* cited by examiner

SYSTEMS AND METHODS OF PRODUCING SYNTHESIS GAS AND BIO-OIL FROM BIOMASS

CROSS-REFERENCE TO RELATED APPLICATIONS

This application is a continuation-in-part that claims priority to U.S. application Ser. No. 63/359,317 filed on Jul. 8, 2022, and U.S. application Ser. No. 17/941,653, filed on Sep. 9, 2022, both entitled SYSTEMS AND METHODS OF PRODUCING BIO-OIL FROM BIOMASS, which are both hereby incorporated by reference in their entirety.

BACKGROUND

Generally, the current practice for biomass gasification is to process biomass directly, such as without extensive pre-processing of the biomass. The technology for this direct bio-gasification is immature, and is thus economically inefficient relative to comparatively mature and decades-old technology associated with the processing of coal in high pressure coal gasification facilities, for example. There are several factors associated with the economic inefficiencies of direct bio-gasification. In particular, voluminous biomass has a low-energy density such that large amounts of biomass are typically needed to feed and maintain operation of current bio-gasifiers. Thus, the inherent low-energy density of the biomass generally limits the economy of scale of such bio-gasifiers. In addition, gasifiers designed for biomass processing typically operate at or around atmospheric pressure. This low-pressure operation is generally implemented due to the various technical challenges of feeding high-pressure biomass gasifiers, thereby limiting the throughput of the gasifier.

Aside from the low-energy density of voluminous biomass, transporting large volumes of biomass feed long distances via traditional transportation requires fuel and resources that limit the economy of the overall enterprise, as well as negatively impact its carbon intensity score.

Another issue typically associated with biomass conversion to renewable fuel is the type of biomass material used, including foodstuffs such as corn, soybeans, canola, and sugar cane. While these crops are a technically acceptable feedstock for conversion to bio fuel, there is a social perception that that these crops are more valuable as food for human consumption, that their utilization for producing fuel may have a negative impact on food prices, and that the utilization of arable land to grow biomass feedstock for fuel would be better used to grow food crops exclusively for human consumption.

Accordingly, there are challenges facing current biomass processing systems for use in producing renewable fuels.

BRIEF SUMMARY

One embodiment of the present disclosure concerns a method of producing bio-oil from biomass. The method comprises producing, in a gasification unit, synthesis gas from a carbonaceous feedstock, optionally cooling the synthesis gas discharged from the gasification unit, channeling the synthesis gas towards a hydrothermal processing unit, wherein the hydrothermal processing unit is configured to process a biomass feedstock contained in a pressurized water stream, transferring, in the hydrothermal processing unit, heat from the synthesis gas to the biomass feedstock, and producing a hydrothermal product from the biomass feedstock in the pressurized water stream.

Another embodiment of the present disclosure concerns a biomass processing system. The system comprises a gasification unit configured to produce synthesis gas from a carbonaceous feedstock, and a hydrothermal processing unit comprising a heat exchanger. The hydrothermal processing unit is configured to receive, at the heat exchanger, a biomass feedstock contained in a pressurized water stream, receive, at the heat exchanger, the synthesis gas discharged from the gasification unit, and transfer heat from the synthesis gas to the biomass feedstock to produce a hydrothermal product.

BRIEF DESCRIPTION OF THE DRAWINGS

Various embodiments of the present disclosure are described in detail below with reference to the attached drawing figures, wherein.

Figure 1:
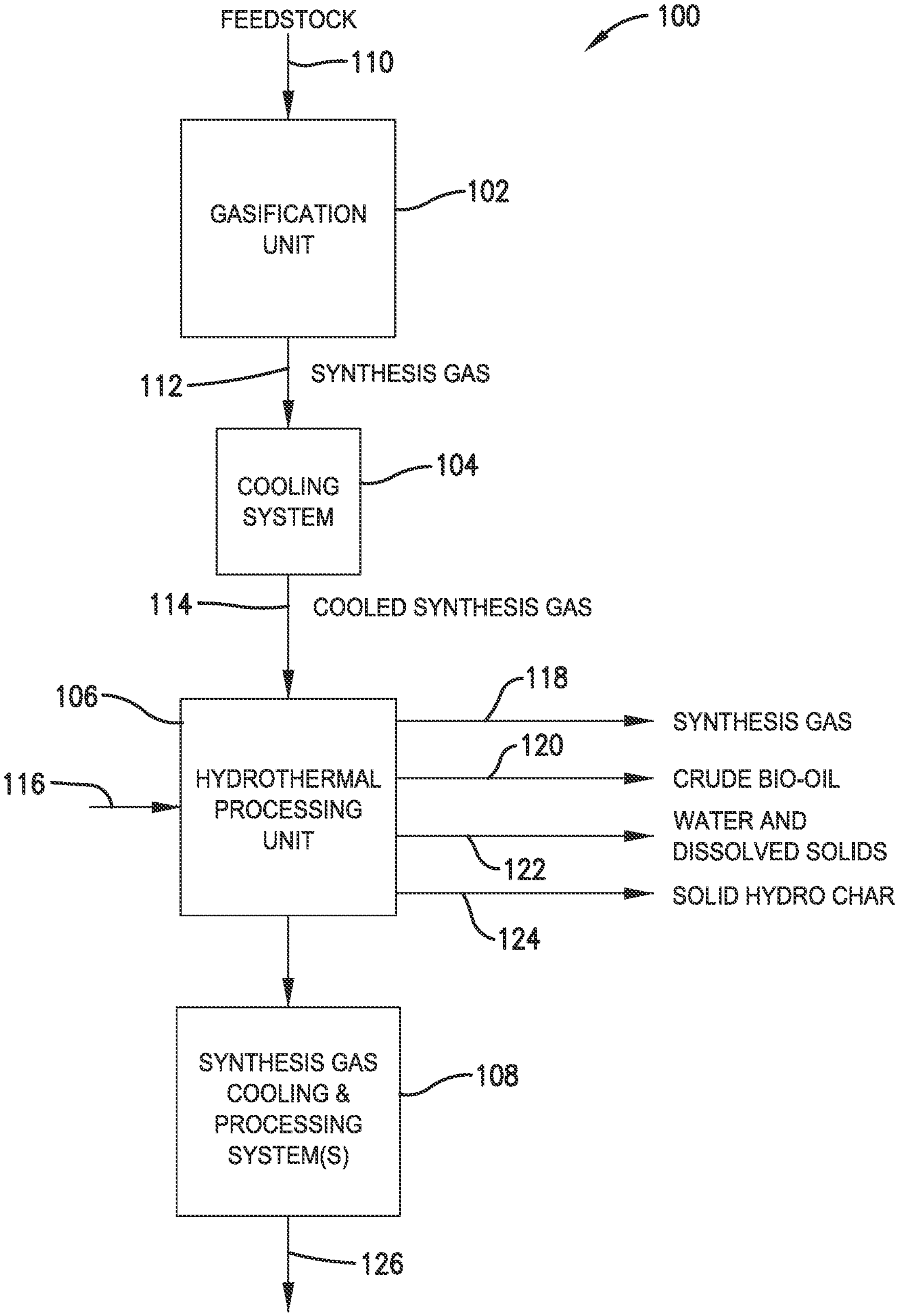
FIG. 1 is an overall schematic flow diagram of a biomass processing system according to various embodiments of the present disclosure.

A more detailed description of various embodiments of the present invention will now be discussed herein with reference to the foregoing drawings. The following description is to be taken by way of illustration and not undue limitation.

DETAILED DESCRIPTION

This disclosure relates generally to bio-oil production and, more specifically, to the economic co-production of synthesis gas and bio-oil, such as from using re-purposed commercial gasifiers typically operable at high temperatures and pressures. The disclosure addresses the challenges in economically extracting lipids and organic carbohydrates from biomass, such as those cultivated specifically for their lipids. One embodiment disclosed herein uses fossil fuel gasification technology that processes fuel such as coal, lignite, petroleum coke, fossil oil, and/or fossil gas via partial oxidation. For example, described herein is a new use for the gasification technology to process non-fossil fuel feeds, such as a "coal-like" feed derived from the pyrolysis, carbonization, torrefaction, hydrothermal carbonization (HTC), hydrothermal liquefaction (HTL), and/or hydrothermal gasification (HTG) of suitable biomass material. This processing of the biomass material releases the volatile components contained therein, such that a concentrated and high energy density solid feed material consisting essentially of the fixed carbon and ash of the original biomass is produced. Desired products, such as crude bio-oil and synthesis gas, may then be converted from this feed material into separately industrially useful commodities, including renewable transportation fuels This concept is based on the idea of synergistic co-production of bio-oil and synthesis gas, originally from gasification of a fossil fuel, using fossil fuel gasification technology. The bio-oil is extracted from biomass, based on techniques such as HTC, HTL, and/or HTG, using the waste heat generated from the gasification of fossil fuel. Unexpectedly, it was found that it is possible to implement this co-production technique completely decoupled from fossil fuels as feedstock. For example, rather than fossil coal, petroleum coke, fossil liquid fuel, or fossil gaseous fuels, the feed to the fossil fuel-type gasifier may be substituted with a biomass derived char (e.g., pyrolysis biochar or hydro-char from HTC, HTL or HTG processes). Thus, fossil fuels may be reduced, minimized, or eliminated as the feed source to a commercial "coal fed" gasifier.

The high temperature and pressure operation of the fossil fuel-type gasifier results in the efficient conversion of fossil fuels and/or biomass-derived feedstocks to synthesis gas. The resultant hot synthesis gas may be quenched against a waste heat radiant boiler, or may be cooled in a direct quench zone by either water, steam, recycled cooled synthesis gas, or any combination thereof, to a temperature below the ash fusion temperature (i.e., approximately 1560-1650° F. (850-900° C.), which should produce ash that is no longer "sticky"). In the embodiments described herein, the resultant cooled synthesis gas may be further cooled in a heat exchanger assembly by transferring heat to lipid-bearing biomass entrained in pressurized water (e.g., at pressures greater than about 400 psig (27.6 bar g)).

This hydrothermal processing of the biomass extracts the lipids, proteins, and other organic carbohydrates therefrom as a crude bio-oil, which is recovered after cooling and decanting. The bio-oil may then be further processed into useful renewable hydrocarbons, including biodiesel, renewable diesel, renewable jet fuel, renewable gasoline, and other renewable transportation fuels. The residual biomass, or hydro-char, may be buried (i.e., sequestered), converted to an agricultural soil supplement such as "Terra Preta," or may be further processed to feed (or partially feed) a repurposed fossil fuel-type gasifier.

When the gasifier's feedstock is derived from biomass, the pressurized synthesis gas may be further processed to other useful commodities, including renewable Fischer-Tropsch products, renewable-methanol, renewable-DME, renewable-gasoline, renewable-ammonia, renewable-synthetic natural gas (SNG), renewable-hydrogen, renewable produced power, or combinations thereof.

The key element of the systems and methods described herein is how the hot synthesis gas, sometimes between about 2200° F. and 2600° F. (1200° C. and 1425° C.), produced from the partial oxidation gasification of a carbonaceous material and then cooled to below the ash fusion temperature or the ash "sticky" temperature, as described above, is used. The cooled synthesis gas leaving the hydrothermal process heat exchanger may have a temperature between about 390° F. and 750° F. (200° C. to 400° C.), and a pressure that is approximately 600 psig (41.45 Bar g). The heat in the partially cooled syngas is used to release, via at least one of the hydrothermal processing techniques described above, the lipids and organic carbohydrates from the biomass cultivated for its lipid content via a hydrolysis enhanced process.

Once most of the lipids and organic carbohydrates have been extracted from the biomass, the extracted components are discharged from the hydrothermal processing unit as a hydrothermal product including bio-oil, water, and produced vapor. When cooled, the bio-oil, water, residual hydro char, and vapor form into a four-phase mixture consisting of a vapor/gas component, a light liquid component, a heavy liquid component, and residual solid hydro-char. The heavy liquid component includes wastewater and some water-soluble dissolved organic carbohydrates and inorganic ash compounds. The lighter liquid phase is the bio-oil. The vapor/gas may be separated from the bio-oil and the water in a three-phase vapor-liquid-liquid separator. The hydro-char may be recovered in the liquid water phase and then separated from the water. The separated residual hydro-char may be further treated, milled, and then fed to the gasifier with the fossil fuel and/or biomass feedstock, can be sequestered as a carbon sink in a landfill, or can be processed into Terra Preta as a soil amendment to improve agriculture.

One objective of the systems and methods described herein is an overall process to capture carbon dioxide directly from the air (Direct Air Capture—DAC), or from a flue stack gas to produce a combination of sustainable transportation fuels, such as biodiesel, renewable diesel, renewable jet fuel, renewable gasoline, and other renewable transportation fuels, all while generating enough power internally from the process to minimize or eliminate utility power consumption, which is typically at least partially produced using fossil fuel.

An amount of the carbon dioxide ($CO_2$) captured from the air, along with water, may be converted into transportation fuel at an approximate or near net neutral overall $CO_2$ emission. Meanwhile, the balance of the $CO_2$ captured from the air may be sequestered in solid form either in a landfill or as carbon bio-char (or hydro-char), which may then be converted to Terra Preta. Alternatively, some of the carbon is recovered as carbon dioxide which may be sequestered as supercritical $CO_2$ disposed in an underground geological formation using the technology disclosed in U.S. Pat. No. 8,585,802, which is hereby incorporated by reference in its entirety.

As discussed above, there are several factors associated with the economic inefficiencies of direct bio-gasification. One way the systems and methods described herein mitigate these economic inefficiencies is by reducing the transportation and costs associated with biochar transportation when compared to the transportation of unprocessed biomass. This is a result of the greater energy density of the biochar produced by the systems and methods described herein. Towards this objective, cultivating the fastest growing biomass in the proximity of the gasification and hydrothermal process will fully or partially eliminate biomass transportation costs. In addition, while it is technically possible to use foodstuff biomass as a feedstock in the systems and methods described herein, one embodiment focuses on the cultivation and use of non-foodstuff biomass grown on non-arable land, or in the ocean. Other sustainable sources of biomass material include waste products such as animal (including human) solid waste, agricultural waste, demolition biomass waste, municipal solid waste, forest waste, old wooden pallets, old railway ties, and the like.

The complete processing train from biomass growth, harvesting, and bio-oil extraction has been uneconomic (or barely economically viable at best) prior to the disclosure of these systems and methods. In addition, the systems and methods described herein provide current owners of gasification process equipment (especially coal gasification process equipment) an environmentally acceptable way to repurpose (or retrofit) their equipment to operate in a more economically and environmentally sustainable manner.

Referring now to the drawings, FIG. 1 is an overall schematic flow diagram of a biomass processing system

100. In the illustrated example, biomass processing system 100 includes a gasification unit 102, a first cooling system 104, a hydrothermal processing unit 106, and a synthesis gas cooling and processing system(s) 108. In operation, gasification unit 102 receives a carbonaceous feedstock 110, and produces synthesis gas 112 from the carbonaceous feedstock 110 via partial oxidation.

As used herein, "carbonaceous feedstock" refers to fossil-based and/or biomass-based carbon feedstocks.

First cooling system 104 receives synthesis gas 112 discharged from gasification unit 102, and if slag (or ash) is present, cools synthesis gas 112, optionally, to below the ash fusion temperature (i.e., within a range between about 850° C. and about 900° C.). If the temperature of synthesis gas 112 is already below the ash fusion temperature, then further cooling may not be needed. Thus, if the synthesis gas 114 is already cool or has optionally been cooled to below the ash fusion temperature, synthesis gas 112 can be processed effectively by equipment of hydrothermal processing unit 106. If needed, the example cooling methods of system 104 include, but are not limited to, radiant boiler heat absorption, quenching with a cold recycled gas stream, steam, or liquid water, or by adding an amount of milled carbonaceous material included in either a liquid water stream (a slurry), or pneumatically transported to the quench zone in a cooled recycled gas stream accompanied by a pressurized steam stream.

Cooled synthesis gas 114 discharged from first cooling system 104 is then channeled towards hydrothermal processing unit 106. Hydrothermal processing unit 106 also receives a biomass feedstock 116 (in a pressurized water stream) for processing therein. Specifically, as will be described in more detail below, hydrothermal processing unit 106 transfers heat from cooled synthesis gas 114 to biomass feedstock 116 to produce a multitude of hydrothermal products, which may be processed into commodities and/or processed and recycled for use in biomass processing system 100. These hydrothermal products include, but are not limited to, additional synthesis gas 118, crude bio-oil 120, water and dissolved solids 122, and solid hydro-char 124. In the example embodiments, hydrothermal processing unit 106 is a hydrothermal liquefaction unit, a hydrothermal carbonization unit, or a hydrothermal gasification unit.

Synthesis gas 114 used to hydrothermally process biomass feedstock 116 is discharged from hydrothermal processing unit 106 and channeled to synthesis gas cooling and processing system(s) 108. As will be described in more detail below, system(s) 108 include one or more processing units for converting synthesis gas 114 into saleable commodities 126, including renewable Fischer-Tropsch products, renewable-methanol, renewable-DME, renewable-gasoline, renewable-ammonia, renewable-synthetic natural gas (SNG), renewable-hydrogen, renewable produced power, or combinations thereof.

Figure 2:
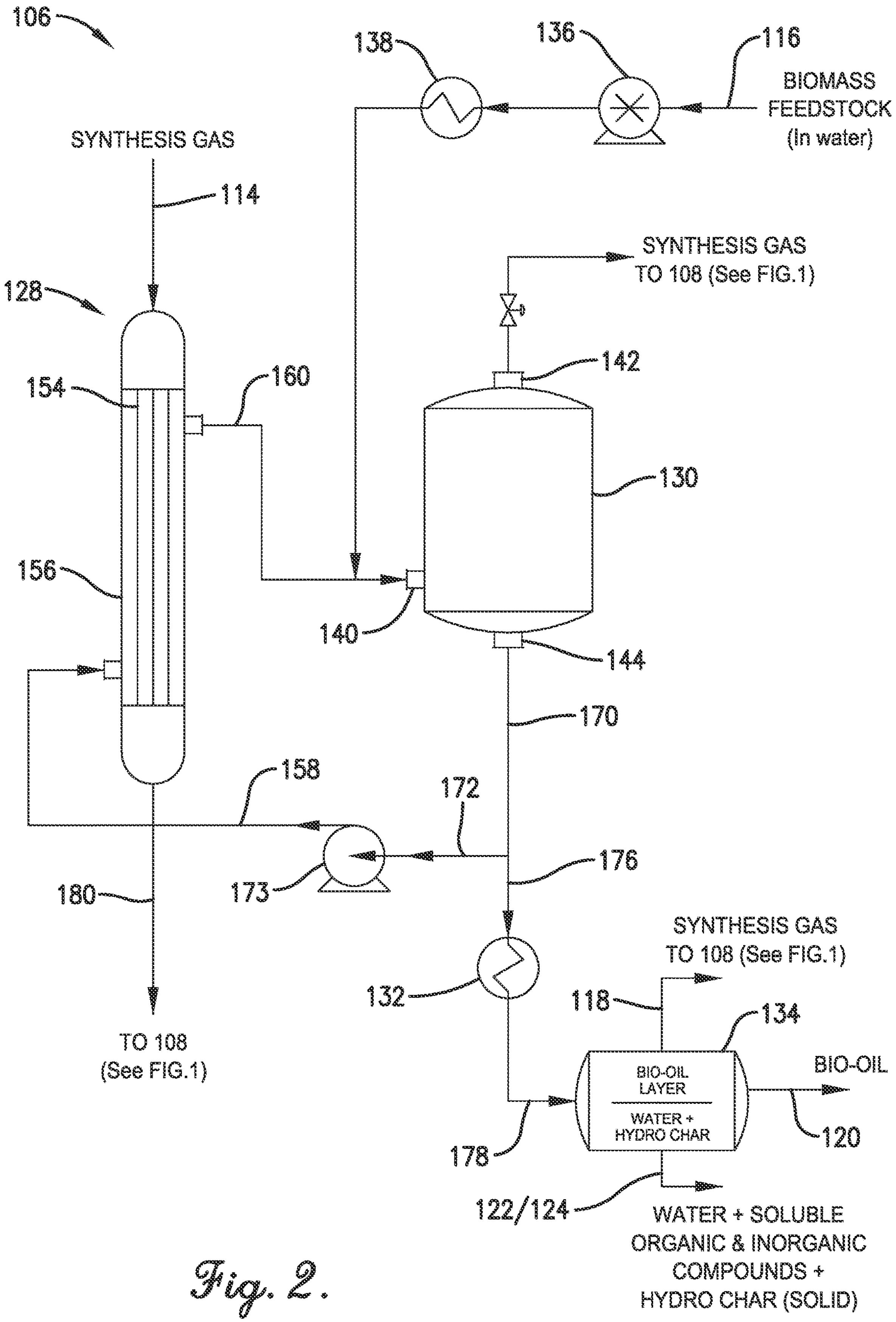
FIG. 2 is a schematic flow diagram of an example hydrothermal processing unit that may be used in the biomass processing system shown in FIG. 1.

FIG. 2 is a schematic flow diagram of one embodiment of hydrothermal processing unit 106. In the illustrated example, hydrothermal processing unit 106 includes a heat exchanger 128, a hydrothermal pressure vessel 130, a second cooling system 132, and a separation vessel 134. In operation, biomass feedstock 116 (in water) is pressurized by a feed pump 136, and heated by a feed preheater 138, before being hydrothermally processed. For example, the heated and pressurized biomass feedstock is channeled to hydrothermal pressure vessel 130, as will be described in more detail below.

Figure 3:
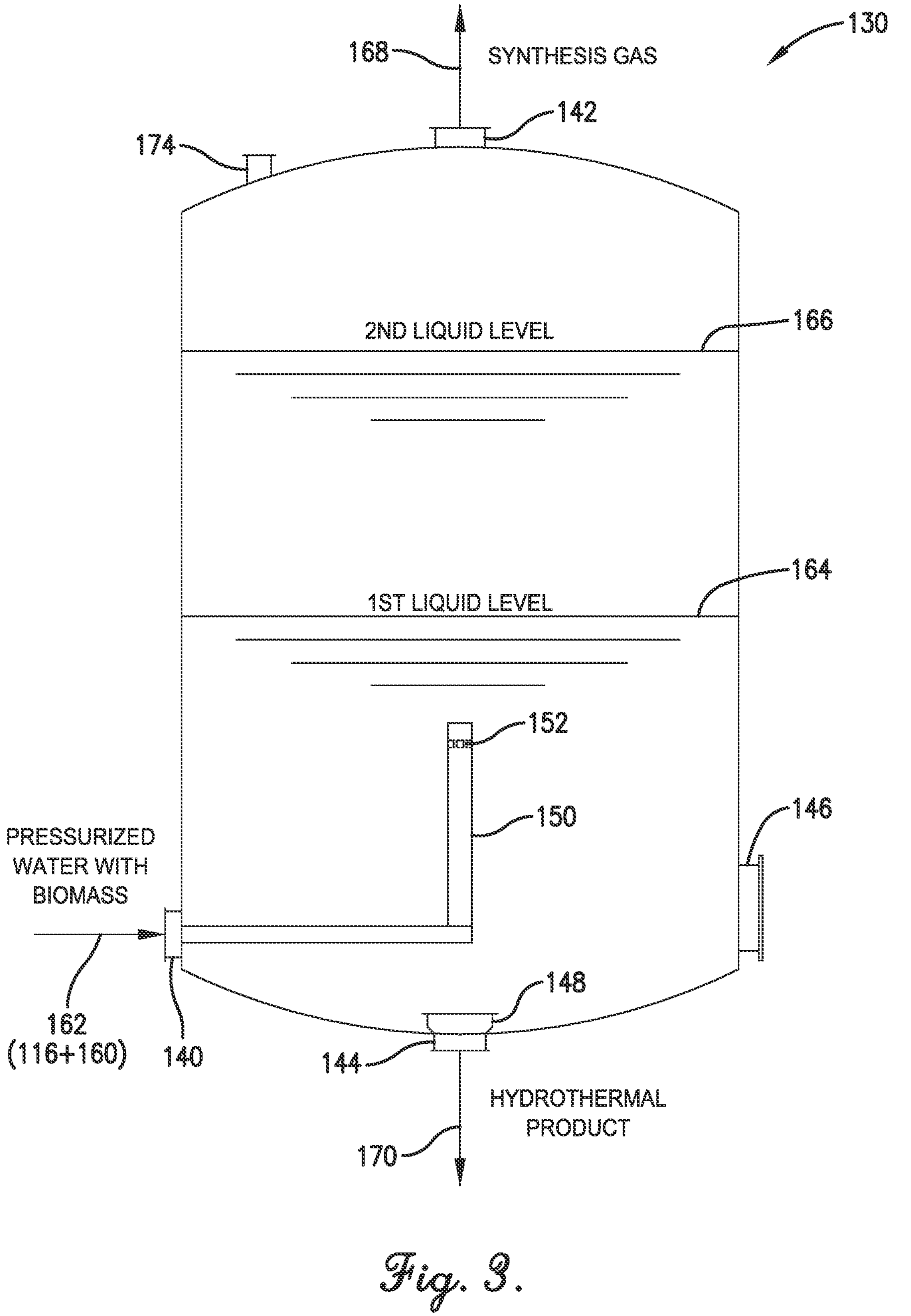
FIG. 3 is a schematic diagram of an example hydrothermal pressure vessel that may be used in the hydrothermal processing unit shown in FIG. 2.

Referring to FIG. 3, hydrothermal pressure vessel 130 includes an inlet 140, a syngas outlet 142, and a hydrothermal product outlet 144. Inlet 140 is oriented to receive biomass feedstock 116 (in water) that has been heated by synthesis gas 114. In some embodiments, recirculated hydrothermal products are also received at inlet 140 for processing within hydrothermal pressure vessel 130. Hydrothermal pressure vessel 130 also includes an access hatch 146 that provides manual access to the interior of the vessel, a vortex breaker 148 positioned at hydrothermal product outlet 144, and a capped stand pipe 150 in flow communication with inlet 140. Capped stand pipe 150 has one or more slots 152 defined therein.

In the illustrated example, slots 152 are defined circumferentially at the top of stand pipe 150 to facilitate radial discharge of feedstock therefrom. Slots 152 may have any size that enables hydrothermal pressure vessel 130 to function as described herein. For example, the size of slots 152 may be based on the size of solid hydro-char particles formed from the hydrothermal processing and that may recirculate within hydrothermal processing unit 106. That is, each respective slot 152 may be sized larger than the solid hydro-char particles to limit blocking the slot openings. In addition, the size and/or number of slots 152 may be selected to adjust the total open slot area on the surface of capped stand pipe 150. The open slot area may be defined within a range between about 50 percent and about 95 percent, between about 70 percent and about 90 percent, or may be approximately 80 percent of the cross-sectional flow area of capped stand pipe 150.

The total slot area is selected based on a desired pressure drop and discharge velocity of products discharged through slots 152. For example, if the total slot area is greater than the cross section of the stand pipe flow area, then the velocity through slots 152 is lower than the velocity through the stand pipe. This will result in a reduced discharge velocity with little to no jet action from slots 152. By constraining the slot total area to be less than the stand pipe cross section area a high velocity jet is discharged from each slot 152. The high velocity jets facilitates mixing the stationary liquid within hydrothermal pressure vessel 130 to form a generally homogeneous mixture. Thus, stratification and formation of unprocessed products is reduced.

As described above, bio-oil may be extracted from biomass using techniques such as HTC, HTL, and/or HTG. The distinction in these processes is based at least partially on the temperature and pressure at which the respective hydrothermal process is performed. From the lowest temperature and pressure to the highest, the hydrothermal processes are ranked from HTC (<248° C.), to HTL (248-375° C.), to HTG (>375° C.). Thus, the respective processes produce different proportions of hydrothermal products, and the hydrothermal process used in a particular biomass production operation may be at least partially based on the desired proportion of hydrothermal products to be produced.

Any biomass feedstock 116 may be fed to hydrothermal processing unit 106 and/or gasification unit 102 that enables biomass processing system 100 to function as described herein. For example, the biomass can either include lipids, or be essentially lipid-free. Example biomass that includes lipids includes, but is not limited to, rapeseed, sunflower, palm, soybean, corn, cottonseed, coconut, peanut, linseed, sesame, almond, aquatic plants such as duckweed and azolla, algae, saltwater algae, seaweed, and kelp. Example biomass that is essentially lipid-free includes, but is not limited to, hard-wood, agriculture waste, building waste, wooden pallets, railroad ties, grasses, municipal solid waste, and animal solid waste.

Generally, the non-lipid biomass types (i.e., those having a moisture content of around 80% by weight or preferably less) are included as candidates for torrefaction, carbonization, or pyrolysis and then used as the substitute for coal in the gasifier, while the biomass containing lipids and is in a dilute suspension with excess water may be used as feedstock for the hydrothermal processes described herein. Thus, efficient use of energy is maintained.

Referring again to FIG. 2, in one example, heat exchanger 128 is a single-pass fire tube and shell assembly having a hot side 154 (tube side) and a cold side 156 (shell side). Hot side 154 receives synthesis gas 114, cold side 156 receives the biomass feedstock in pressurized water stream along with the recirculated hydrothermal products, as will be described in more detail below, and heat is transferred from synthesis gas 114 to the biomass feedstock (e.g., recirculated hydrothermal products) to produce a hydrothermal product 160. Then the heated hydrothermal products in stream 160 heat the preheated fresh biomass feedstock in pressurized water leaving preheater 138 such that heat absorbed by the fresh biomass feed in the combined feed is virtually instantly brought to a desired operating temperature within pressure vessel 130. This optional step is performed to avoid a gradual transition in temperature from the preheater to the desired operating temperature. This fast heat-up facilitates avoiding any possible undesirable reactions of the biomass as it transitions more slowly through a typical continuous heating process. Hot side 154 may be defined by a single pass of multiple parallel tubes oriented vertically, wherein synthesis gas 114 enters a top section of heat exchanger 128 and is discharged from a bottom section thereof. The tube diameter may be selected to define a velocity suitable for both ensuring the solids do not flow too slowly to plug the tubes, and to facilitate heat transfer across the tube from synthesis gas 114 (inside the tubes) to the surrounding hydrothermal liquid product slurry in the shell.

Hydrothermal product 160 discharged from heat exchanger 128 is channeled to hydrothermal pressure vessel 130, along with biomass feedstock 116, to continue the processing thereof. More specifically, referring again to FIG. 3, hydrothermal product 160 and biomass feedstock 116 are discharged into hydrothermal pressure vessel 130 through slots 152 in stand pipe 150. This combined fluid 162 fills hydrothermal pressure vessel 130 to any desired liquid level that enables biomass processing system 100 to function as described herein. The liquid level may be adjustable to modify the residence time of combined fluid 162 within hydrothermal pressure vessel 130. For example, combined fluid 162 may be maintained at a first liquid level 164 or a second liquid level 166 that is higher than first liquid level 164. Accordingly, the residence time of combined fluid 162 is greater at second liquid level 166 than at first liquid level 164.

A first portion 172 of a hydrothermal product 170 discharged from hydrothermal pressure vessel 130 is pressurized and recirculated by a pump 173 towards cold side 156 of heat exchanger 128 (via line 158) for continued processing therein. The heated recirculated flow is heated and maintained at a higher predefined operating temperature associated with the desired hydrothermal process to be performed within vessel 130. The slightly higher temperature enables the mixed flow (116+160) temperature to be set at a temperature desired in vessel 130 to process this particular biomass and to provide the economic optimal splits between crude bio-oil, hydro char, and the additional synthesis gas 168 to be combined with the synthesis gas leaving heat exchanger 128 at stream 180. The temperature of the recirculated flow may be adjusted by controlling the flow of fresh preheated biomass (in pressurized water) that is fed to hydrothermal pressure vessel 130. As described above, the variable residence time is adjusted based on the liquid operating level within hydrothermal pressure vessel 130. In the example embodiment, hydrothermal pressure vessel 130 includes a level gauge sensor 174 that monitors the liquid level and provides feedback for determining the flow of hydrothermal products to feed second cooling system 132.

Second cooling system 132 is positioned to receive a second portion 176 of hydrothermal product 170, and to cool second portion 176 to define a multi-phase mixture 178 within separation vessel 134. Multi-phase mixture 178 includes synthesis gas 118, crude bio-oil 120, water and dissolved solids 122, and solid hydro-char 124 (i.e., solid carbonaceous material). Separation vessel 134 separates multi-phase mixture into its component parts such that a gas phase (synthesis gas 118), a liquid phase (crude bio-oil 120), and a liquid/solids phase (water and dissolved solids 122 and solid hydro-char 124) are discharged from separation vessel 134 from respective outlets.

In one embodiment, a portion of multi-phase mixture 178, such as some or all of at least one of the liquid products resulting from the cooling step, is channeled through a hydraulic turbine 177 to recover power.

Synthesis gas 118 may include short-chain hydrocarbons and non-condensable gases such as light paraffinic hydrocarbons, hydrogen, carbon monoxide, carbon dioxide, and nitrogen. This gas stream may be combined with the syngas stream 180 leaving the hot side of the heat exchanger.

As will be described in more detail below, the solid carbonaceous material may be processed to produce feedstock for use in biomass processing system 100. In addition, the dissolved solids generally include organic and/or inorganic compounds (e.g., organic carbohydrates and inorganic ash). As will be described in more detail below, the organic and/or inorganic compounds may be used to facilitate production of feedstock for use in biomass processing system 100. Synthesis gas 180 discharged from heat exchanger 128 may be processed by synthesis gas cooling and processing system(s) 108 (shown in FIG. 1), as will be described in more detail below.

Figure 4:
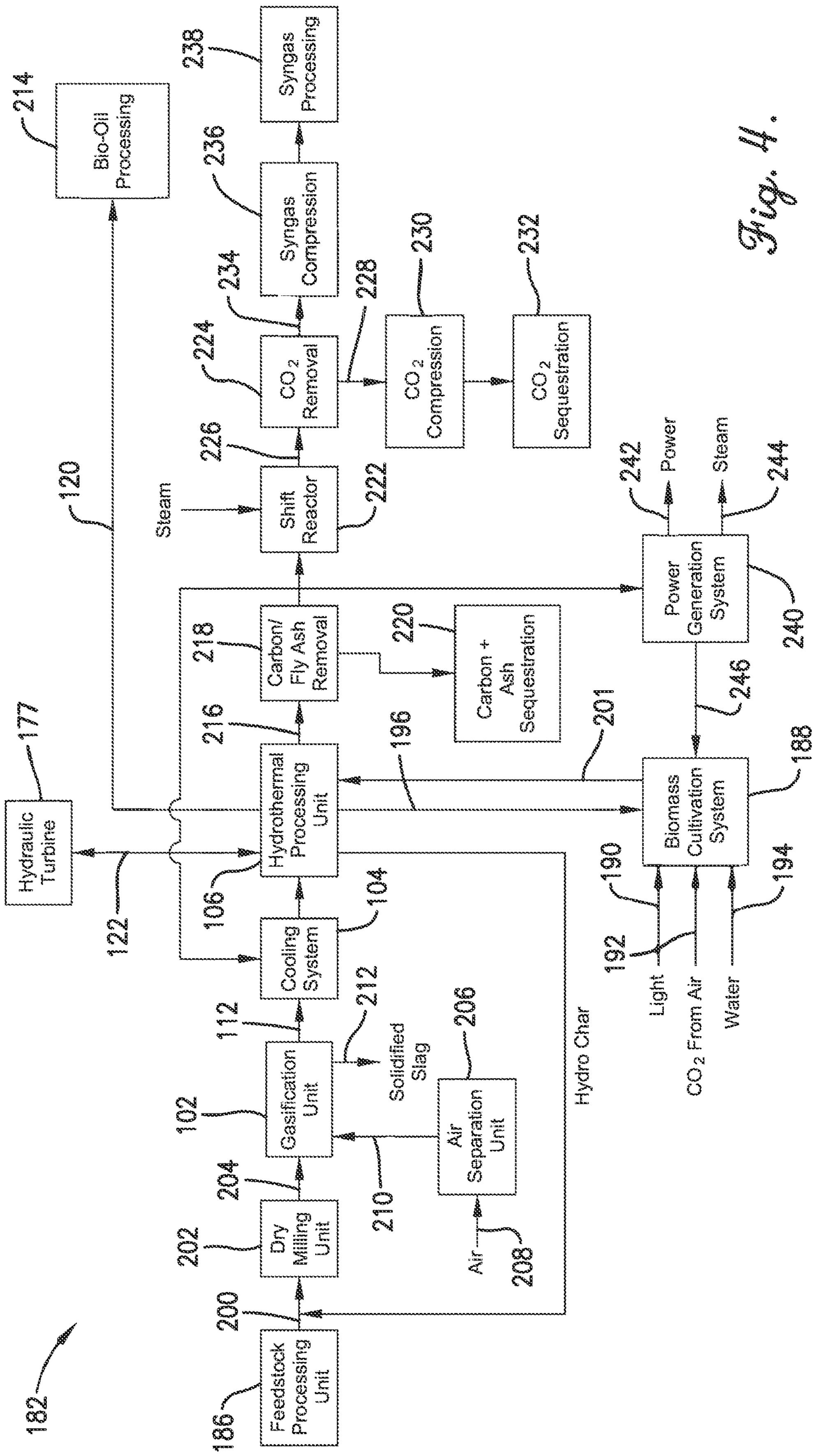
FIG. 4 is a schematic flow diagram of an example biomass processing system in accordance with FIG. 1.
Figure 5:
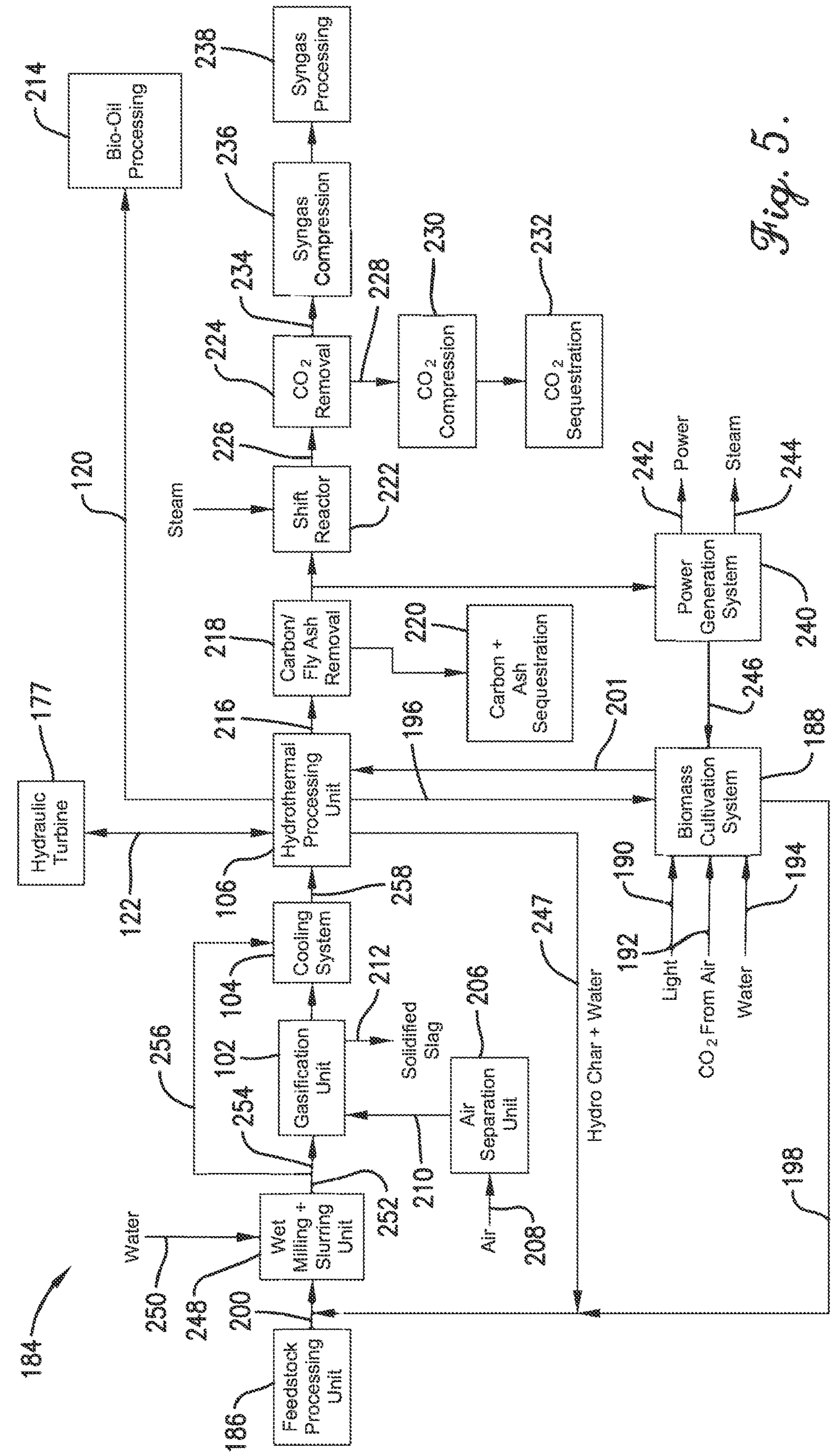
FIG. 5 is a schematic flow diagram of another example biomass processing system in accordance with FIG. 1.

FIGS. 4 and 5 are schematic and more detailed flow diagrams of example biomass processing systems 182 (FIG. 4) and 184 (FIG. 5) in accordance with FIG. 1. For example, biomass processing systems 182 and 184 include gasification unit 102, first cooling system 104, and hydrothermal processing unit 106. In some embodiments, the additional units shown in FIGS. 4 and 5 support and/or supplement operation of the units shown in FIG. 1.

For example, referring to FIG. 4, biomass processing system 182 further includes a feedstock processing unit 186. In the illustrated example, feedstock processing unit 186 is operable to pretreat cultivated biomass, for example, for conversion to a suitable feedstock for processing in gasification unit 102. Feedstock processing unit 186 may process the biomass in at least one of a torrefaction, carbonization, pyrolysis, hydrothermal carbonization, hydrothermal liquefaction, or hydrothermal gasification process. In an alternative example, the feedstock provided to gasification unit 102 is a fossil-fuel based material.

Torrefaction, carbonization, and pyrolysis processes, for example, are performed under nominal atmospheric pressure and at progressively higher temperatures, respectively, in the absence of air in a kiln. The volatile material leaving the kiln in a torrefaction, carbonization, or pyrolysis process includes vaporized water, short chain hydrocarbons, and non-condensable gases such as hydrogen, carbon monoxide, carbon dioxide, and nitrogen. This stream may be cooled and partially condensed. The hydrocarbon liquid product absent the volatile material may be recovered as a potential bio-oil. This bio-oil thus may augment the production of bio-oil produced in hydrothermal processing unit 106.

Alternatively, HTC, HTL and HTG are processes that pretreat the biomass in the presence of heated pressurized water. Each of these methods facilitates removing volatile matter from the untreated biomass to form residual carbonaceous coal-like material. The volatile matter removed ultimately ends up in either the gas and/or liquid phase. The residual carbonaceous coal-like material contains mostly carbon, a variable amount of unremoved volatile matter, and ash. Accordingly, feedstock processing unit 186 pretreats the biomass to make it friable and capable of being milled to meet particular commercial high-pressure gasifier licensor feedstock specifications. It should be noted that it is not essential to remove all volatile material from the biomass, but rather only enough volatile matter needs to be removed to accomplish milling of the solid material to meet the specifications of the solid feedstock set by a gasifier licensor.

In general, torrefaction, carbonization, and pyrolysis can be used to process biomass having a limited moisture content, and HTC, HTL, and HTG can be used when the biomass is very diluted with excess water (e.g., micro or macroalgae). The need for removing excess water in the first three methods is energy intensive and generally uneconomical. In addition, adding large quantities of water needed to process biomass with a low moisture content in the second three methods is also uneconomical.

In the illustrated example, biomass processing system 182 includes a biomass cultivation system 188 that produces biomass organisms that may be used to produce at least some of the feedstock fed to gasification unit 102. Biomass cultivation system 188 grows biomass organisms using light 190 (e.g., sunlight or artificial light), carbon dioxide 192 from the air, and water 194. In addition, as described above, water and dissolved solids 122 (shown in FIG. 2) is separated from the produced bio-oil and discharged from hydrothermal processing unit 106 in a distinct stream. Thus, in one embodiment, a portion of the water 196 in water and dissolved solids 122 is removed, and this portion having organic and/or inorganic compounds dissolved therein is channeled to biomass cultivation system 188. The organic and/or inorganic compounds may then be used by the biomass organisms being produced therein in growth.

The organic portion of dissolved solids leaving the hydrothermal processing unit 106 typically contains organic aldehydes, organic acids and organic salts. These compounds are used by the growing algae in their growth as it contributes to the carbon intake of the cells. The inorganic dissolved matter includes ammonium compounds and phosphorous compounds, which are necessary nutrients to the cultivation system. The absence of these inorganic components will require the addition of these nutrients at some expense. Minimizing the need for purchasing fresh nutrients is therefore a desirable outcome to the enterprise. Some additional nitrogenous nutrients can be specifically produced by cultivating azolla, since azolla is one of the uniquely high productivity biomass plants capable of fixing nitrogen from the air and delivering ammonium compounds to the water, which in term can be consumed by the algae in its growth. Azolla also is a prolific fern capable of producing a large fraction of lipid producing biomass. There are other trace inorganic compounds that are recycled with the water component leaving the hydrothermal unit 106. Any shortfall of trace inorganic compounds in the cultivation system 188 will need to be purchased and added according to the requirements for optimizing algae growth. The trace components are necessary but not expensive due to the low quantity needed.

In addition, biomass in water 201 may be channeled from the biomass cultivation system 188 to hydrothermal processing unit 106. The hydrothermal processing unit 106 produces crude bio-oil, synthesis gas, and hydro char, which may be dried and recycled to the milling unit 202. The hydro char could also be totally or in part sequestered either in a landfill, or used as an agriculture soil additive.

Hydrothermal carbonization of microalgae, for example, produces a hydro-char with properties not unlike a low rank coal, such as lignite. The hydro-char is derived from the protein and carbohydrate fractions of the microalgae. The volatile matter consists mostly of the lipids. These lipids can be separated and processed in transesterification reactions to produce bio-diesel and glycerin.

However, hydrothermal liquefaction may convert all (or most) of the lipids, proteins, and carbohydrates in the microalgae at higher temperatures to produce crude bio-oil and to leave behind a smaller fraction of residual solid coal-like material as compared to hydrothermal carbonization. This crude bio-oil product may be processed similar to fossil crude oil via hydro treatment and separation into different refinery products, typically in a refinery designed to process fossil crude oil. Depending on the source of biomass, the hydrothermal carbonization may not produce a solid material that is friable enough and amenable to milling. In such circumstances, the temperature of the hydrothermal process may be increased. In other words, the minimum processing temperature of the hydrothermal process performed may vary based on the type of biomass starting material being pretreated.

At temperatures greater than about 375° C., gasification of the bio-oil begins to occur, which breaks the bio-oil down and produces a gas phase including synthesis gas. Feedstock processing unit 186 and/or hydrothermal processing unit 106 may be operated at these increased temperatures when the production of additional synthesis gas is a desired objective. The ranking of progressively increasing hydrothermal process severity is summarized as follows: 1) HTC produces the most hydro-char and the least bio-oil; 2) HTL produces more bio-oil liquids than HTC and less solid hydro-char; and 3) HTG produces more synthesis gas at the expense of crude bio-oil production. Plant optimization in maximizing profit will determine the temperature at which to operate feedstock processing unit 186 and/or hydrothermal processing unit 106 to produce more hydro-char, more bio-oil, or even more synthesis gas.

It should be noted that HTC, HTL, and HTG are approximate labels to describe the process regimes. Site specific operations will be chosen to determine which temperature should be used to maximize enterprise profit. Different sites will determine their own respective operating temperatures.

Once formed, solid carbonaceous material 200 is channeled to a dry milling unit 202 (FIG. 4) for processing therein. For example, dry milling unit 202 mills solid carbonaceous material 200 to a particle size in accordance with particular commercial high-pressure gasifier licensor feedstock specifications. Thus, dry milling unit 202 produces a milled feedstock 204 that is then channeled to gasification unit 102 for processing therein, as described above. Alternatively, or in addition to solid carbonaceous material 200, a solids phase discharged from hydrothermal processing unit 106 (i.e., solid hydro-char 124 (shown in FIG. 1)) may be channeled to dry milling unit 202, as described above.

Specifically, biomass processing system 182 further includes an air separation unit 206 that intakes air 208, separates oxygen 210 from air 208, and selectively channels oxygen 210 to gasification unit 102 for processing therein. That is, the amount of oxygen 210 provided to gasification unit 102 is controlled to limit combustion, and to facilitate partial oxidation of milled feedstock 204. This partial oxidation reaction produces synthesis gas 112 and, after cooling, solidified slag 212. Synthesis gas 112 may be channeled to first cooling system 104 and then channeled to hydrothermal processing unit 106 for processing therein, as described above.

Crude bio-oil 120 produced in hydrothermal processing unit 106 is discharged from separation vessel 134 (FIG. 2), as described above. In the illustrated example, crude bio-oil 120 may then be transported for bio-oil processing 214. The bio-oil processing 214 may include, but is not limited to, hydro-processing and/or transesterification.

For example, the recovered crude bio-oil may be sent to a refinery for hydro-processing to produce a renewable crude bio-oil, and then further processed to produce renewable gasoline, renewable diesel, or renewable jet, etc. Generally, the refinery operations needed for bio-oil processing are Fluid Cat Cracker (FCC) and hydrotreating. Alternatively, the crude bio-oil may be treated onsite through a process known as transesterification, which produces bio-diesel and glycerin. In this example, the extracted lipid oil is processed with an alcohol and either an acid or a base. For example, methanol may be combined with either sodium hydroxide or potassium hydroxide to transesterify the bio-oil directly to bio-diesel and glycerin. The glycerin may be sold or recycled for use in biomass processing system 100. In some embodiments, the methanol used for transesterification may be produced by, and readily available from, operation of biomass processing system 100, such as from the processing of synthesis gas.

In the illustrated example, synthesis gas 216 that has been cooled within hydrothermal processing unit 106 is then processed in a manner that is normal and consistent with a gasifier licensor's typical process lineup. For example, this cooled syngas can be further treated in at least one of carbon and fly ash removal 218 (e.g., with cyclones and/or candle filter) followed by carbon and ash sequestration 220, syngas cooling, syngas scrubbing, or in a shift reactor 222. Processing synthesis gas in a CO-shift reaction converts carbon monoxide to carbon dioxide and hydrogen to increase the hydrogen content of the synthesis gas (followed by acid gas removal, designed to remove $CO_2$). Carbon dioxide capture 224 may be performed on the hydrogen-rich stream 226 discharged from shift reactor 222, and carbon dioxide 228 captured therefrom may be compressed 230 to recover the carbon dioxide in either its vapor or liquid phase. When in the liquid phase, for example, carbon dioxide may then be pumped to supercritical pressure and sequestered 232 (stored) in a geological formation, as described in U.S. Pat. No. 8,585,802.

The treated and cooled synthesis gas 234 may then be further compressed 236 and then further processed 238 into saleable commodities, such as renewable hydrogen, ammonia, Substitute Natural Gas (SNG), Fischer-Tropsch products, methanol, and/or gasoline etc, in any combination that facilitates improving the economic viability of biomass processing system 100.

In the illustrated example, biomass processing system 100 further includes a power generation system 240, such as a simple cycle, a Rankine cycle, or a combined cycle power plant. In one embodiment, synthesis gas produced in biomass processing system 100 may also be channeled to power generation system 240 to enable power 242 and/or steam 244 to be produced therefrom, thereby improving the overall economic viability of biomass processing system 100. In one embodiment, flue gas 246 generated by power generation system 240 may be used to facilitate growth of biomass organisms in biomass cultivation system 188. For example, as described above, biomass cultivation system 188 grows biomass organisms using, among other things, carbon dioxide 192 extracted from the air via biomass direct air capture, for example. In addition, flue gas 246 containing a higher concentration of carbon dioxide may be channeled to biomass cultivation system 188 to augment the carbon dioxide used to help further produce the biomass organisms, thereby improving the economic viability of biomass processing system 100. For example, the carbon dioxide from flue gas 246 may be supplied as a sub-surface bubbled gas within the biomass cultivation system 188.

In general, the most prolific method of producing biomass containing lipids is through the growth of micro or macroalgae. Algae can be produced in freshwater or treated wastewater. There are also strains of algae suitable for use as biomass feedstock that can grow in saltwater (brackish water or sea water). Some of the fresh water (terrestrial based) algae may be grown by biomass cultivation system 188 and then provided as feedstock to gasification unit 102 and/or hydrothermal processing unit 106, as will be described in more detail below.

Other nutrients needed by land-based, fresh-water algae for growth are nitrogenous compounds (such as ammonia, or urea as examples) and a phosphorous component, such as Single Super Phosphate (SSP) or Triple Super Phosphate (TSP). Accordingly, in one embodiment, biomass cultivation system 188 produces both algae and azolla. Azolla is a freshwater fern that produces a lipid product, and that is capable of "fixing" nitrogen from the ambient environment. Thus, in one embodiment, the algae and azolla being grown in biomass cultivation system 188 are co-located relative to each other in the same facility, which enables the nitrogen compounds produced by the azolla to be used by the growing algae. Accordingly, the cost of purchasing a nitrogenous growth element is reduced or eliminated. The phosphates may be contained in the recycled wastewater stream following HTC, HTL, or HTG extraction. In this case, the wastewater is recycled at least in part to an algae growth media. The wastewater used in a final synthesis gas wash step also contains ammonia, which can be channeled to further provide nitrogen compounds for the algae growth feedstock.

Referring now to FIG. 5, this hydro-char-water mixture 247 is recycled for processing to become partial or complete feedstock for gasification unit 102. In the illustrated embodiment, at least a portion of biomass organisms 198 grown by biomass cultivation system 188 may be combined with hydro-char-water mixture 247 discharged from hydrothermal processing unit 106. Thus, adjusting the amount of water 250 needed to make a slurry in the wet milling unit 248 to have a suitable solid carbonaceous/water concentration for the slurry fed gasifier as specified by the gasifier vendor.

In the example illustration, biomass processing system 184 includes a wet milling and slurring unit 248 positioned upstream from gasification unit 102. Solid carbonaceous material 200 is channeled to wet milling and slurring unit 248 for processing therein. Alternatively, or in addition to solid carbonaceous material 200, hydro-char-water mixture 247 and biomass organisms 198 may also be channeled to wet milling and slurring unit 248. Optionally, water 250 may be added to this combined unprocessed feedstock, and wet milling and slurring unit 248 mills the combined unprocessed feedstock to produce a concentrated specified feedstock slurry 252. The milling may be performed with a wet rod mill, a wet ball mill, and the like.

In the illustrated example, a first portion 254 of feedstock slurry 252 is channeled to gasification unit 102 for processing therein, and a second portion 256 of feedstock slurry 252 is channeled to first cooling system 104. Specifically, first cooling system 104 uses feedstock slurry 256 to cool (i.e., quench) synthesis gas 112 discharged from gasification unit 102. In some embodiments, this process of transferring heat from synthesis gas 112 to feedstock slurry 252 hydrogasifies feedstock slurry 252 to produce synthesis gas 258. Accordingly, the synthesis gas yield of biomass processing system 100 may be increased without requiring additional oxygen consumption, while simultaneously facilitating a reduction in temperature of synthesis gas 112 to below the ash fusion temperature.

Figure 6:
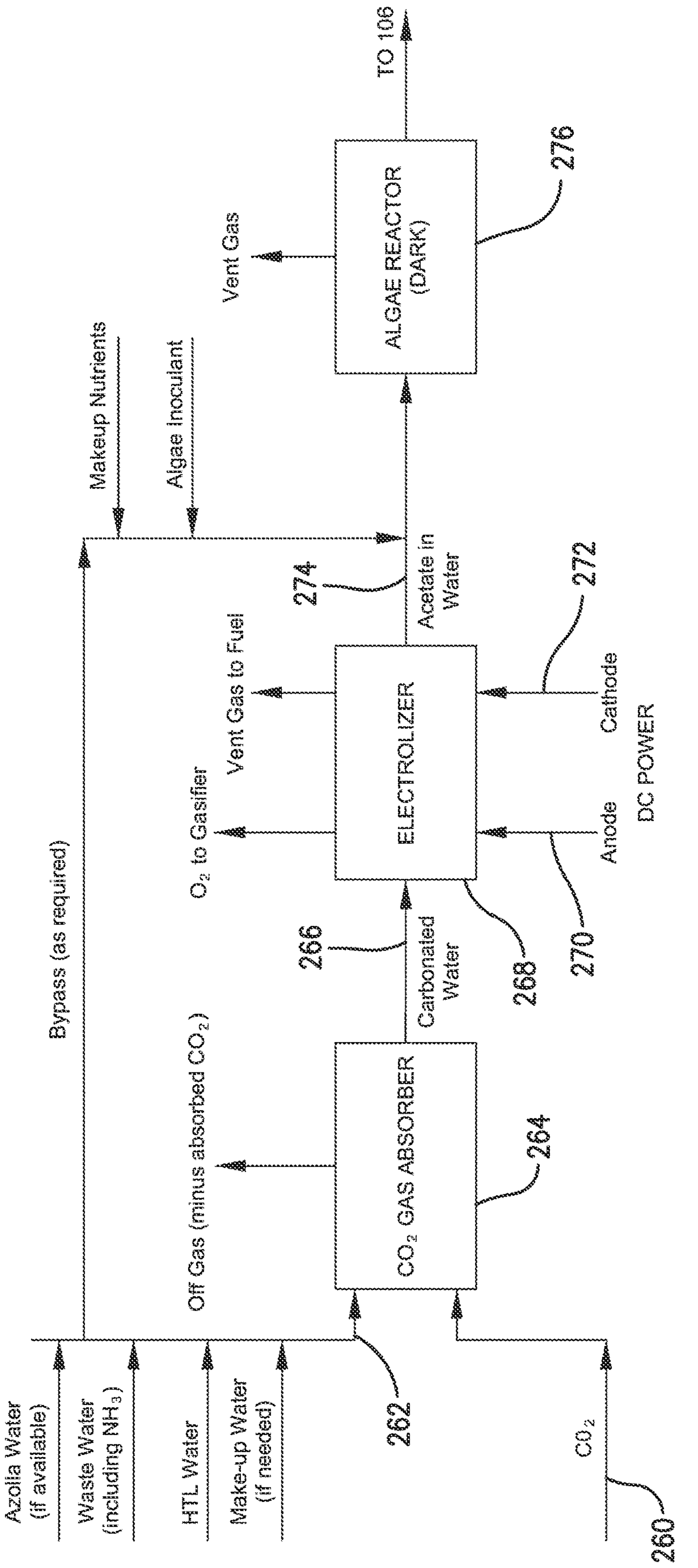
FIG. 6 is a schematic flow diagram of an alternative biomass growth system that may be used in the biomass processing systems shown in FIGS. 4 and 5.

Referring now to FIG. 6, $CO_2$ may be captured from a gas stream 260 via absorption in a pressurized water stream 262. Water stream 262 may be formed from water from hydrothermal processing unit 106, waste water, azolla water (if available), and any additional make-up water (if needed). Gas stream 260 and pressurized water stream 262 are combined at a $CO_2$ gas absorber 264 to produce a pressurized carbonated water stream 266. Carbonated water stream 266 is then channeled to a pressurized electrolyzer 268, which is designed to facilitate the conversion of carbonated water to form organic compounds, including acetates. The electrolyzer includes an anode 270 and a cathode 272. Electrolyzer 268 subjects carbonated water stream 266 to electrolysis where oxygen is given off at anode 270, and acetate is formed at cathode 272. Oxygen released in this process is used to displace oxygen from the air separation plant (which is a feed to the gasifier), to facilitate off-setting the cost of electrical power in the production of oxygen. Cathode 272 forms two carbon atom organic compounds, such as ethanol and mostly an acetate, in an acetate stream 274 fed to an algae reactor 276. These organic compounds can be used as carbonaceous feed to cause algae to grow in algae reactor 276, even in a dark environment. This algae growth process is known as heterotrophic growth in contrast to photoautotrophic growth, which is a more common growth mechanism that uses light such as sunlight or artificial light.

As used herein, "pressurized" in reference to the water stream, the carbonated water stream, and/or the electrolyzer means any pressure that is greater than atmospheric pressure. In general, the higher the pressure the greater amount of carbon dioxide that can be held within water.

Algae reactor 276 may be a dark CSTR (Continuous Stirred Tank Reactor). Cultivating algae in this manner may provide an economic advantage to biomass processing systems 182 and 184 as compared to photo-bio-reactors or an aerated open pond (or raceway) typically used for the industrial growth of algae. This is because the algae growth requiring suitable light (such as sunlight or artificial light) is self-limiting as the light penetration depth is limited due to the algae closest to the light source blocks more light from reaching inside, further from the light source.

Further, in the absence of light, growth in this embodiment is not adversely impacted and can be continuous when designed to grow in the dark.

This disclosure relates generally to crude bio-oil production and, more specifically, to the economic co-production of synthesis gas and crude bio-oil. This disclosure enables hydrothermal processing of biomass to be a viable economic process. Without this disclosure, known biomass processing systems generally have a comparatively high capital expenditure (CAPEX) and operating expenditure (OPEX). In addition, the added value of the recovered bio-oil from the gasification operation is a significant added economic benefit to the enterprise.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The invention claimed is:

1. A method of producing bio-oil from biomass, the method comprising:

producing, in a gasification unit, synthesis gas from a carbonaceous feedstock;

optionally cooling the synthesis gas discharged from the gasification unit;

channeling the synthesis gas into a hydrothermal processing unit, wherein the hydrothermal processing unit processes a biomass feedstock contained in a pressurized water stream;

transferring heat from the synthesis gas to a product recirculation stream in the hydrothermal processing unit in at least one heat exchanger to provide a cooled synthesis gas stream and a heated product recirculation stream; and producing a hydrothermal product from at least a portion of the heated product recirculation stream;

further comprising, prior to the producing, combining at least a portion of the biomass feedstock contained in pressurized water stream with the heated product recirculation stream to provide a combined feed stream and introducing the combined feed stream into a hydrothermal pressure vessel;

withdrawing an initial hydrothermal product stream from the hydrothermal pressure vessel and dividing the initial hydrothermal product stream into a first portion and a second portion, wherein the first portion comprises the product recirculation stream and the second portion comprises the hydrothermal product, and wherein the hydrothermal product comprises at least one product chosen from synthesis gas, crude bio-oil, water and dissolved solids, or solid hydro char.

2. The method in accordance with claim 1, wherein the method comprises cooling the synthesis gas discharged from the gasification unit to a temperature of about 900° C. or less via at least one of radiant boiler heat absorption or quenching with a cold recycled gas stream, steam, or liquid water.

3. The method in accordance with claim 1, wherein producing a hydrothermal product comprises producing the hydrothermal product in at least one of a hydrothermal carbonization process, a hydrothermal liquefaction process, or a hydrothermal gasification process.

4. The method in accordance with claim 1 further comprising:

cooling the hydrothermal product to define a multi-phase mixture that comprises crude bio-oil and other hydrothermal products; and separating the crude bio-oil from the other hydrothermal products.

5. The method in accordance with claim 4 further comprising hydro-processing the crude bio-oil to produce renewable transportation fuels.

6. The method in accordance with claim 4 further comprising processing the crude bio-oil via transesterification to produce bio-diesel and glycerin.

7. The method in accordance with claim 4, wherein the hydrothermal products comprise solid carbonaceous material, the method further comprising at least one of:

sequestering the solid carbonaceous material;

converting the solid carbonaceous material to an agricultural soil supplement; or channeling the solid carbonaceous material to the gasification unit for processing therein.

8. The method in accordance with claim 7 further comprising:

milling the solid carbonaceous material to produce a milled feedstock; and channeling the milled feedstock to the gasification unit for processing therein.

9. The method in accordance with claim 7 further comprising:

adding water to the solid carbonaceous material;

wet milling the solid carbonaceous material to define a feedstock slurry;

channeling a first portion of the feedstock slurry to the gasification unit for processing therein;

transferring heat from the synthesis gas discharged from the gasification unit to a second portion of the feedstock slurry, wherein the second portion of the feedstock slurry is heated to hydrogasify the solid carbonaceous material and produce additional synthesis gas; and optionally cooling the additional synthesis gas to a temperature of about 900° C. or less.

10. The method in accordance with claim 7, wherein the solid carbonaceous material is entrained in water to define a hydro-char-water mixture, the method further comprising:

removing a portion of the water from the hydro-char-water mixture, wherein the portion of the water has at least one of organic or inorganic compounds dissolved therein; and using the organic or inorganic compounds to help grow biomass organisms.

11. The method in accordance with claim 4 further comprising channeling a portion of the multi-phase mixture through a hydraulic turbine to recover power.

12. The method in accordance with claim 1 further comprising:

processing the synthesis gas to convert carbon monoxide to carbon dioxide and hydrogen;

and one or both of:

capturing and then pressurizing the carbon dioxide to supercritical pressure for sequestration in a geological formation; and using the captured carbon dioxide to augment biomass cultivation.

13. The method in accordance with claim 1, wherein the transferring heat further comprises maintaining the temperature of the biomass feedstock in the pressurized water stream for a duration that enables crude bio-oil to be extracted from the biomass feedstock aided by a hydrolysis reaction.

14. The method in accordance with claim 1, wherein the carbonaceous feedstock comprises a biomass material, the method further comprising:

processing the biomass material before being received at the gasification unit, wherein the processing produces a solid carbonaceous product;

milling the solid carbonaceous product to produce a milled feedstock; and channeling the milled feedstock to the gasification unit for processing therein.

15. The method in accordance with claim 14 further comprising:

adding water to the solid carbonaceous product before being milled;

wet milling the solid carbonaceous product to define a feedstock slurry; and channeling a first portion of the feedstock slurry to the gasification unit for processing therein.

16. The method in accordance with claim 15 further comprising transferring heat from the synthesis gas discharged from the gasification unit to a second portion of the feedstock slurry, wherein the second portion of the feedstock slurry is heated to produce a gasified slurry, and wherein the synthesis gas is cooled, optionally, to a temperature of about 900° C. or less.

17. The method in accordance with claim 1 further comprising processing biomass organisms to produce at least one of the carbonaceous feedstock or the biomass feedstock, wherein at least a portion of the biomass organisms are cultivated heterotrophically.

18. The method in accordance with claim 17, further comprising:

producing water-soluble organic compounds by absorbing carbon dioxide into a pressurized water solvent, and hydrolyzing the carbonated water via electrolysis; and using the water-soluble organic compounds to produce the biomass organisms used in the processing step.

19. The method in accordance with claim 18, wherein at least a portion of the pressurized water solvent is received from the hydrothermal processing unit.

20. The method in accordance with claim 18, wherein the hydrolysis is performed at a cathode of an electrolyzer to produce the water-soluble organic compounds comprising an acetate and other organic compounds.

21. The method in accordance with claim 18, further comprising growing the water-soluble organic compounds heterotrophically.

22. The method in accordance with claim 1, further comprising:

generating, with a power generation system, power with a portion of the synthesis gas discharged from the hydrothermal processing unit, wherein the power generation system also produces flue gas from a combustion process; and using the captured carbon dioxide to produce biomass organisms at least one of heterotrophically or photoautotrophically.

23. The method in accordance with claim 1, further comprising:

processing biomass organisms to produce at least one of the carbonaceous feedstock or the biomass feedstock, wherein the biomass organisms comprise algae and azolla; and cultivating the biomass organisms by co-locating the algae and azolla to enable compounds produced by the azolla to be used by the algae in growth.

24. The method of claim 1, wherein the at least one heat exchanger comprises a hot side for receiving the synthesis gas and discharging the cooled synthesis gas, a cold side for receiving the product recirculation stream and discharging the heated product recirculation stream, wherein heat from the synthesis gas is transferred from the hot side of the heat exchanger to the cold side of the heat exchanger, and further comprising transferring heat from the heated product recirculation stream to the biomass feedstock contained in pressurized water stream in the hydrothermal processing unit during the combining of at least a portion of the biomass feedstock contained in pressurized water stream with the heated product recirculation stream to provide the combined feed stream.

25. The method of claim 1, wherein the hydrothermal product comprises solid hydro char and further comprising introducing at least a portion of the solid hydro char into the gasification unit.

* * * * *